United States Patent [19]

Neti et al.

[11] Patent Number: 4,655,900

[45] Date of Patent: Apr. 7, 1987

[54] METHOD FOR TREATING ELECTRODES AND IMPROVED ELECTROCHEMICAL CELL

[75] Inventors: Radhakrishna M. Neti, Brea; John N. Harman, III, Placentia, both of Calif.

[73] Assignee: Beckman Industrial Corporation, La Habra, Calif.

[21] Appl. No.: 837,802

[22] Filed: Mar. 10, 1986

[51] Int. Cl.⁴ .................. G01N 27/46; B05D 3/02
[52] U.S. Cl. .................... 204/415; 204/402; 204/280; 427/383.7; 427/125
[58] Field of Search ............ 204/415, 1 P, 402, 280; 427/383.7, 372.2, 125

[56] References Cited

U.S. PATENT DOCUMENTS

| | | | |
|---|---|---|---|
| 2,328,101 | 8/1943 | Rosenblatt | 427/383.7 |
| 3,134,697 | 5/1964 | Neidrach | 429/30 |
| 3,265,526 | 8/1966 | Beer | 427/383.7 |
| 3,432,355 | 3/1969 | Neidrach et al. | 429/42 |
| 3,470,019 | 9/1969 | Steele | 427/383.7 |
| 3,510,420 | 5/1970 | Mills | 204/415 |
| 3,824,167 | 7/1974 | Oswin et al. | 204/432 |
| 4,051,006 | 9/1977 | Neti et al. | 204/415 |
| 4,186,071 | 1/1980 | Romine et al. | 204/402 |
| 4,248,908 | 2/1981 | Saito et al. | 427/383.7 |

Primary Examiner—T. Tung
Attorney, Agent, or Firm—Plante, Strauss & Vanderburgh

[57] ABSTRACT

An improved electrochemical cell is described which comprises at least one electrode having increased signal strength achieved by treating at least the working surface of the electrode with a coating of a polytetrafluoroethylene and a catalyst metal selected from the group consisting of platinum and the oxides thereof in an aqueous oligosaccharide solution. Following coating, the electrode is heated to a temperature below the sintering temperature of the polymer to thermally convert the oligosaccharide in the presence of the catalyst metal and drive off the conversion products. An electrode thus treated exhibits a substantially inproved signal strength as compared to an electrode of the same construction which has not been treated in accordance with the invention.

14 Claims, 2 Drawing Figures

METHOD FOR TREATING ELECTRODES AND IMPROVED ELECTROCHEMICAL CELL

FIELD OF THE INVENTION

The present invention relates to electrochemical cells and electrodes therefor and more particularly to a method for increasing the output signal strength of electrodes in such electrochemical cells.

BACKGROUND OF THE INVENTION

In recent years the demand for cleaner breathing environments, both in the atmosphere and in specific breathing environments, has led to the development of improved methods for measuring specific gasses in atmospheres. Of special interest has been the need for a safe, reliable and portable instrument which can be taken into the field for the detection and measurement of components in gasses. For example, carbon monoxide conventionally has been measured by infrared techniques, however, the expense and inconvenience of infrared equipment render its use under ordinary field conditions impractical at the present time. Electrochemical techniques are most readily adaptable for relatively inexpensive, reliable, portable instrumentation. U.S. Pat. No. 4,051,006 and the references discussed therein provides in more detail background information on the development of portable instrumentation for the detection and measurement of contaminants such as carbon monoxide, hydrogen sulfide, nitric oxide, unsaturated hydrocarbons and other noxious gasses in the atmosphere.

As discussed in U.S. Pat. No. 4,051,006 a major problem with electrochemical devices has been the low signal magnitude developed by instruments sized for portability. This normally results in the requirement for large amplification means and an inherent lack of stability and response.

Accordingly, it would be desireable to provide an improved electrode for use in such portable instruments which is capable of developing increased output current thereby enabling the use of smaller amplification means and minimizing the size of the instrument.

SUMMARY OF THE INVENTION

In accordance with the invention an improved electrochemical cell comprises electrodes disposed in an electrochemically inert enclosure having porous membrane sealed openings. The enclosure is filled with an electrochemically inert, hydrophilic material, such as glass wool, throughout which a suitable electrolyte is dispersed to provide a portable electrochemical cell constructed in accordance with U.S. Pat. No. 4,051,006.

The electrode for use in the cell is produced by applying a layer comprising a suspension of catalyst metal comprising platinum or its oxides and polytetrafluoroethylene in an aqueous oligosaccharide solution to at least the working surface of the electrode. After applying the suspension, the electrode is heated to a temperature sufficiently high to thermally convert the oligosaccharide in the presence of the catalyst metal and drive off the conversion products but below the sintering temperature of the polytetrafluoroethylene to provide a coating of polymer/catalyst metal which unexpectedly results in a working surface for the electrode capable of developing an output signal substantialy more powerful than the output signal developed by an electrode constructed in the same manner but not treated with the oligosaccharide containing suspension. In the preferred embodiment of the invention the improved electrode is of the type produced by pressing platinum black onto a platinum/iridium screen as disclosed in U.S. Pat. No. 4,051,006. However, in accordance with the invention the catalyst metal/polymer suspension can also be deposited directly on an electrode surface comprising a noble metal or other conductive material or on an essentially non-conductive substrate such as a polymer membrane.

DESCRIPTION OF THE PREFERRED EMBODIMENT

Figure 1:
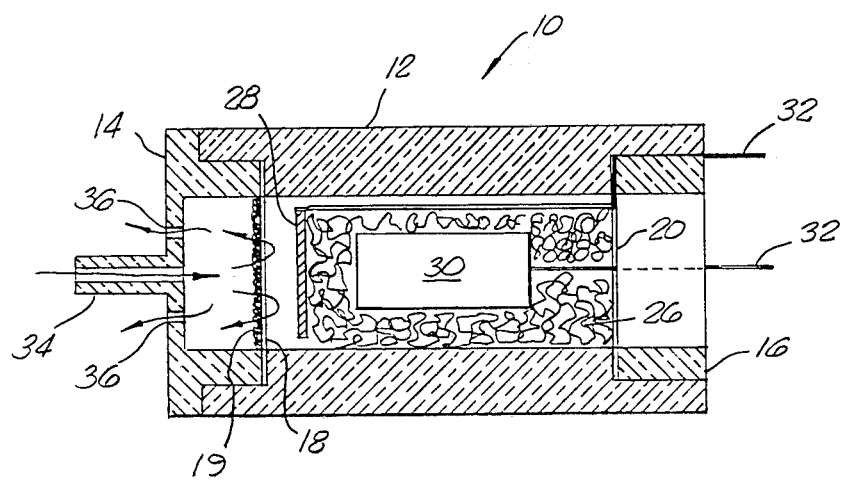
FIG. 1 is a cross section through a cell employing two electrodes treated in accordance with the invention.

FIG. 1 illustrates a typical electrochemical cell utilizing at least one electrode treated in accordance with the invention in which the cell 10, functioning as an amperometric cell as is well known in the art, is shown having an open ended cylindrical body 12. A cap 14 is affixed to one end of the body 12 and a collar 16 is affixed to the opposite end. The body 12, the cap 14 and the collar 16 are formed from an electrochemically inactive material such as polytetrafluoroethylene. A first porous membrane 18 is held in place across one opening of the body 12 by the cap 14. A second porous membrane 20 is held in place across the opening at the opposite end of the body 12 by the collar 16. The membranes 18 and 20, in conjunction with the body 12, define an electrolyte reservoir 24 containing an electrochemically inert, hydrophilic filler material 26 such as glass wool saturated with a suitable electrolyte such as sulfuric or phosphoric acid. The membranes 18 and 20 may be formed from any of the porous polymeric materials available in the art and excellent results have been achieved using expanded polytetrafluoroethylene having a pore size of 0.1 to 10 microns and a high pore density such as that sold by W. L. Gore and Associates under the trademark Gore-Tex No. 3 and Gore-Tex No. 4. An anode 28 and a cathode 30 are disposed in the interior of the body 12 and retained therein by the filler material 26. Additionally, a reference electrode (not shown) may be provided. The anode 28 is disposed so that its working surface is adjacent to but not in contact with the membrane 18. The term "working surface" is used herein to refer to the electrode surface adjacent the membrane and which is exposed to the test gas. The placement of the cathode 30 within the interior of the body 12 is not critical but has been found to work well when placed approximately in the center of the body 12, as shown, to prevent touching other electrical surfaces in the event of shock or vibration. Wires 32 provide electrical connection between the electrodes 28 and 30 and a source of potential, not shown. The cap 14 is provided with an inlet tube 34 and outlet openings 36, the total cross sectional area of which is less than the cross sectional area of the inlet tube so that as gas being tested is introduced through the inlet tube under slight pressure, the difference in flow rates through the inlet tube and the outlet openings will cause a slight positive pressure against the membrane 18. This slight positive pressure is sufficient to permit the test gas to permeate the membrane 18 and contact the working surface of the anode 28. The second membrane 20 permits the by-products of the electrochemical reactions to exit the interior of the body 12 thereby to prevent contamination and attendant reduction in cell response.

The cell as described is sensitive to a number of gasses and therefore to make the cell sensitive to a specific gas an appropriate scrubber is utilized to prevent contaminants from contacting the working surface of the anode 28. For the purpose of this description the cell is designed to detect and measure carbon monoxide. Accordingly a layer of silver oxide 19 is deposited on the exterior surface of the membrane 18 to remove unwanted contaminants and thus make the system sensitive to CO only.

Figure 2:
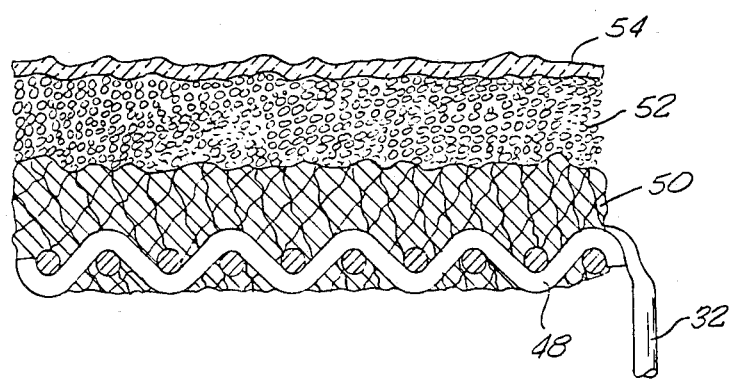
FIG. 2 is a cross section, in enlarged scale, of one of the electrodes of FIG. 1.

A preferred electrode construction is illustrated in FIG. 2 in which the electrode is constructed in accordance with the teachings of U.S. Pat. No. 4,051,006 and is further treated in accordance with the present invention to provide an anode 28 which produces a substantially increased output signal. For the purpose of illustrating the invention the following description will refer to an electrode one centimeter in diameter. It should be clear, however, that the preparation of larger or smaller electrodes can be extrapolated from the description that follows.

A one centimeter diameter platinum/iridium wire screen 48 is cut and the wire 32 is welded thereto. The mesh size of the screen 48 can range between 30 mesh up to 200 mesh. Good results are achieved when the screen comprises 90% platinum and 10% iridium although acceptable results are obtained using platinum or palladium as the screen composition. Two to 20 milligrams of platinum black 50 are pressed onto the screen 48 at ambient temperature at a pressure of 500 to 3,000 psi. The improved electrode for use in the cell is produced by applying a layer comprising a suspension of platinum or an oxide thereof, preferably platinum black, and polytetrafluoroethylene in an aqueous oligosaccharide solution to at least the working surface of the electrode. After application of the suspension, which may be by any suitable means such as by spraying or brushing, the electrode is heated to a temperature sufficiently high to thermally convert the oligosaccharide in the presence of the platinum and drive off the conversion products but below the sintering temperature of the polytetrafluoroethylene thereby to provide a coating 52 of polymer/platinum or platinum oxide which unexpectedly results in a working surface for the electrode capable of developing an output signal of up to 20 times more powerful than the output signal developed by an electrode constructed in the same manner but not treated with the oligosaccharide containing suspension in accordance with the invention. This temperature will range from between about 80° C. to about 200° C. The layer 52 may be protected by an overcoat of a thin layer 54 of polytetrafluoroethylene. In accordance with the invention there is thus formed on the surfaces of the electrode so treated a thin, porous but coherent coating 52 comprising platinum or platinum oxide and polytetrafluoroethylene. Moreover, the electrode so treated exhibits an improved signal strength. The oligosaccharide solution may incorporate any of the soluble mono-, di-, and trisaccharides in aldo or keto form and soluble starch. For example, sucrose, glucose, lactose and maltose are among the more readily available oligosaccharides which can be used in the present invention. In addition, soluble starch, which is a polysaccharide is also useful in the present invention because it is soluble in water as contrasted to the rest of the polysaccharides which are water insoluble and therefore not useful in the invention.

The concentration of the oligosaccharide in the aqueous solution portion of the suspension is not critical provided that at least an effective amount of the oligosaccharide is utilized in concentrations which do not weaken the finished coating on the electrode surface. Good results are achieved with an oligosaccharide concentration of between about 0.1% and about 5% In this example the suspension comprises a solution of 3 gm of sucrose in 500 ml of demineralized water to which is added a dispersion of polytetrafluoroethylene in the ratio of one part of polymer to twenty five parts of the sucrose solution. The suspension also includes 0.002 gm to about 0.005 gm of platinum black per milliliter of sucrose solution.

Although it is not fully understood, the temporary presence of the oligosaccharide in the catalyst metal/polymer suspension increases in some manner the activity of the working surface of the electrode so as to increase the signal output 10 to 20 times over the signal output of an equivalent electrode which has not been treated in accordance with the invention. Thus, for example, two electrodes prepared in exactly the same manner as described above except that one electrode was coated with a suspension which did not contain the oligosaccharide produced an output current of between 0.04–0.08 microamperes when contacted by a nitrogen stream containing 50 ppm CO. The other electrode treated with a catalyst metal/polymer suspension in an aqueous sucrose solution in accordance with the invention produced a signal of about 0.8 microamperes when exposed to the same test gas.

While the improved electrode of the invention has been described in connection with an improved electrochemical cell for the detection of CO, it will be understood that the electrode is used in cells for the detection of other contaminants such as hydrogen sulfide, and the like. As is well understood in the art, the composition of the scrubber material on the membrane 18 can be altered to prevent the passage of CO and to permit a different contaminant gas to pass into contact with the working surface of the anode of the cell. Other scrubber materials include carbon black and activated charcoal as well as mercuric chloride which is useful in cells for the determination of $H_2S$. In addition the selectivity of the cell for a particular test substance can be determined by the potential at which the cell is operated and the selection of the electrolyte in accordance with known technology.

While a preferred embodiment and modifications of the invention have been described in the foregoing description and illustrated in the drawings, it will be understood that minor changes may be made in the details of construction as well as in the combination and arrangement of parts without departing from the spirit and scope of the invention as claimed.

We claim:

1. In an electrochemical cell including an electrochemically inert body defining an electrolyte reservoir and having porous membrane sealed openings, an electrolyte disposed in said body and at least a first and second electrode disposed in said body, said first electrode being disposed adjacent to and in non-contacting relationship with one of said membrane sealed openings and having a working surface for contacting a test gas permeating said porous membrane, the improvement comprising having at least the working surface of at least said first electrode treated by coating with a suspension comprising a catalyst metal and polytetrafluoroethylene in an aqueous oligosaccharide solution and heating said working surface below the sintering temperature of said polytetrafluoroethylene to thermally convert said oligosaccharide in the presence of the catalyst metal and to drive off said conversion products thereby to increase the signal strength of said electrode so treated.

2. The electrochemical cell of claim 1 wherein said oligosaccharide solution comprises saccharides selected from the group consisting of water soluble monosaccharides, disaccharides, trisaccharides and water soluble starch.

3. The electrochemical cell of claim 1 wherein said oligosaccharide is selected from the group consisting of sucrose, glucose, lactose, maltose and soluble starch.

4. The electrochemical cell of claim 1 wherein said oligosaccharide solution comprises sucrose.

5. The electrochemical cell of claim 1 wherein said catalyst metal is selected from the group consisting of platinum and the oxides thereof.

6. The electrochemical cell of claim 1 wherein the working surface of said second electrode has been treated by coating with said suspension of catalyst metal and polytetrafluoroethylene in an aqueous oligosaccharide solution and heating to a temperature below the sintering temperature of polytetrafluoroethylene.

7. The electrochemical cell of claim 1 further including a reference electrode, the working surface of which has been treated by applying a coating of said suspension thereon and heating below the sintering temperature of said polytetrafluoroethylene.

8. The electrochemical cell of claim 1 wherein the concentration of said oligosaccharide in said aqueous suspension is between about 0.1% and about 5%.

9. A method for treating at least a surface of an electrode to increase the signal strength of said electrode comprising the steps of:
  (a) coating said working surface with a suspension of finely divided catalyst and polytetrafluoroethylene in an aqueous solution of sucrose, said catalyst being selected from the group consisting of platinum and platinum black; and
  (b) heating said working surface to a temperature sufficient to thermally convert said oligosaccharide in the presence of said catalyst and below the sintering temperature of said polytetrafluoroethylene.

10. The method of claim 9 wherein said working surface is heated to a temperature of between 80° C. and 200° C.

11. The method of claim 9 wherein said oligosaccharide is selected from the group consisting of sucrose, glucose, lactose, maltose and soluble starch.

12. The method of claim 9 wherein said oligosaccharide is sucrose.

13. The method of claim 12 wherein said aqueous sucrose solution contains between about 0.1% and about 5% sucrose.

14. The method of claim 9 wherein said aqueous sucrose solution contains 1% sucrose.

* * * * *